United States Patent [19]

Jessel, Jr. et al.

[11] Plant 4,341

[45] Dec. 5, 1978

[54] CHRYSANTHEMUM PLANT

[75] Inventors: Walter H. Jessel, Jr., Grantsville, W. Va.; William E. Duffett, Salinas, Calif.

[73] Assignee: Yoder Brothers, Inc., Barberton, Ohio

[21] Appl. No.: 870,256

[22] Filed: Jan. 17, 1978

[51] Int. Cl.[2] ..... A01H 5/00

[52] U.S. Cl. ..... Plt./78

[58] Field of Search ..... Plt./78

*Primary Examiner*—Robert E. Bagwill

*Attorney, Agent, or Firm*—Beall & Jeffery

[57] ABSTRACT

A spider capitulum type of chrysanthemum plant which is a sport of the cultivar Splash, disclosed in our pending U.S. application Ser. No. 778,667, filed Mar. 17, 1977, and now U.S. Plant Pat. No. 4,218, splatter being distinguished from the parent cultivar by its medium yellow ray floret color.

1 Drawing Figure

The present invention comprises a new and distinct cultivar of *Chrysanthemum morifolium*, Ramat., hereinafter referred to by the cultivar name of Splatter (#73038601).

Splatter is a product of planned sport induction program which had the objective of expanding the color range of the parental cultivar, Splash (#73038048); disclosed in our pending U.S. application Ser. No. 778,667, filed Mar. 17, 1977, and now U.S. Plant Pat. No. 4,218.

Splatter was discovered and selected by William E. Duffett and Walter H. Jessel, Jr. on June 8, 1976 as one plant within a flowering block of Splash in a controlled environment in Barberton, Ohio. Plants within the flowering block were derived from stock plants which had been irradiated as rooted cuttings with an x-ray source of 2600 r units.

The first act of asexual reproduction of Splatter was accomplished when vegetative cuttings were taken from the initial selection in September, 1976 in a controlled environment in Barberton, Ohio by a technician working under formulations established and supervised by Walter H. Jessel, Jr. and William E. Duffett. Horticultural examination of selected units initiated Dec. 1, 1976 has demonstrated that the combination of characteristics as herein disclosed for Splatter are firmly fixed and are retained through successive generations of asexual reproduction.

Splatter has not been observed under all possible environmental conditions. The phenotype may vary significantly with variations in environment such as temperature, light intensity and daylength. The following observations, measurements, and comparisons describe plants grown in Salinas, Calif. under greenhouse environmental conditions which approximate those generally used in commercial practice.

The following traits have been repeatedly observed and are determined to be basic characteristics of Splatter which in combination distinguish this chrysanthemum as a new and distinct cultivar:

(1) Spider capitulum type.

(2) Flat capitulum form.

(3) Medium yellow ray floret color.

(4) Diameter across face of inflorescence ranging from 100 to 115 mm. at maturity.

(5) Uniform ten week photoperiodic flowering response to short days.

(6) Tall plant height (requires 2-4 long day weeks prior to short days to attain a flowered plant height of 77 to 82 cm. when grown as a single stem plant for November through April flowerings.

(7) Semi-upright branching pattern.

The accompanying color photographic drawing shows typical inflorescence and foliage characteristics of Splatter. Some difficulty was encountered in obtaining accurate color representation, the photographic rendition being more gold or less yellow than the actual flower color of Splatter. The color readings within the following description are, however, correct.

Of the many commercial cultivars known to the present inventors, the most similar existing cultivars in comparison to Splatter are the parental cultivar Splash and Super Yellow (#66506003; unpatented). Reference is made to attached Chart A which compares certain characteristics of Splatter with the same characteristics of Splash and Super Yellow. General comparisons are as follows:

(1) In comparison to Splash, Splatter has different ray floret color. Other characteristics of Splatter are similar to those same characteristics of Splash.

(2) In comparison to Super Yellow, Splatter has different ray floret color, smaller diameter across face of capitulum, and taller plant height. The branching pattern, flowering response period, capitulum form, and capitulum type of Splatter are similar to those same characteristics of Super Yellow.

In the following description, color references are made to A Limit Color Cascade, published by the Munsell Company, 1972 edition. The color values were determined between 11:30 and 11:55 A.M. on Nov. 30, 1977 under 80 foot-candle light intensity at Salinas, Calif.

Botanical Classification: *Chrysanthemum morifolium*, Ramat., cv Splatter.

I. INFLORESCENCE

A. Capitulum:

*Form.*—Flat.

*Type.*—Spider.

*Permanence.*—14 to 18 days.

*Diameter across face.*—100 to 115 mm.

B. Corolla of ray florets:

*Color (abaxial).*—25-5 to 25-3.

*Color (immature center).*—21-2 to 21-1.

*Color (adaxial).*—26-2 to 26-3.

C. Reproductive organs:

*Androecium.*—Present disc florets; scant to numerous; scant pollen.

*Gynoecium.*—Present both ray and disc florets.

II. PLANT

A. General appearance: Semi-upright branching pattern; tall height.

B. Foliage:

*Color (abaxial).*—Approximately 20-14.

*Color (adaxial).*—Approximately 21-14 overlaid with white.

We claim:

1. A new and distinct cultivar of *Chrysanthemum morifolium;* Ramat., known by the cultivar name Splatter and particularly characterized as to uniqueness by the combined characteristics of spider capitulum type; flat capitulum form; medium yellow ray floret color; diameter across face of capitulum from 100 to 115 mm. at maturity; uniform 10 week flowering response to photoperiodic short-day control; tall plant height; and semi-upright branching pattern.

* * * * *

CHART A

COMPARISON OF SPLATTER, SPLASH, AND SUPER YELLOW

| CULTIVAR | RAY FLORET COLOR | DIAMETER ACROSS FACE OF CAPITULUM | PLANT HEIGHT | BRANCHING PATTERN | FLOWERING RESPONSE PERIOD | CAPITULUX FORM AND TYPE |
|---|---|---|---|---|---|---|
| Splatter | Medium Yellow | 100 to 115 mm. | Tall, 77 to 82 cm. | Semi-upright | 10 week | Flat Spider |
| Splash | White | 100 to 115 mm. | Tall 77 to 82 cm. | Semi-upright | 10 week | Flat Spider |
| Super Yellow | Light Yellow | 100 to 115 mm. | Short 60 to 70 cm. | Semi-upright | 10 week | Flat Spider |

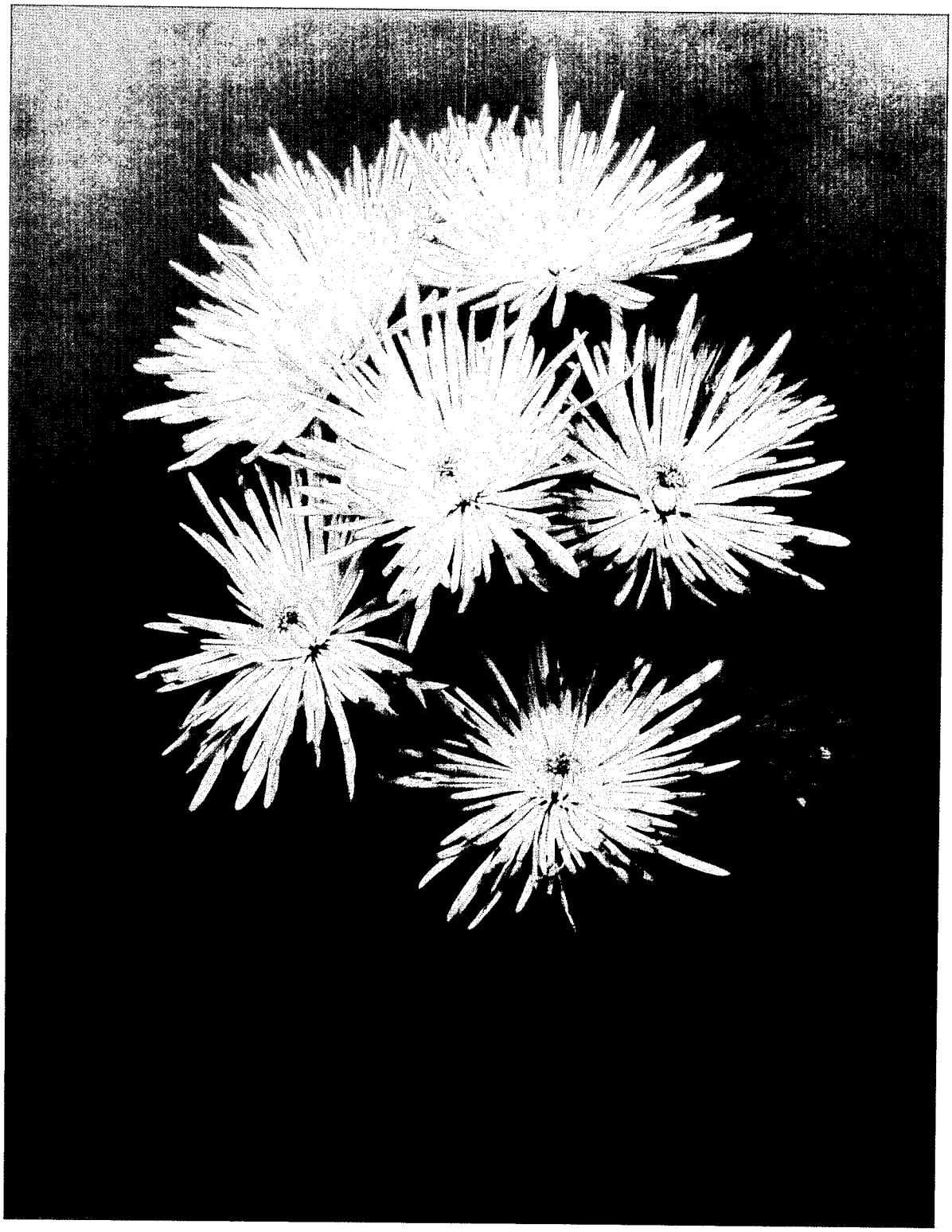

COMPARISONS MADE OF PLANTS GROWN IN A GREENHOUSE IN SALINAS, CALIFORNIA.